US009555077B2

(12) United States Patent
Murakami et al.

(10) Patent No.: US 9,555,077 B2
(45) Date of Patent: Jan. 31, 2017

(54) METHODS OF LOWERING BODY TEMPERATURE BY ADMINISTRATION OF DESACYL GHRELIN OR ITS DERIVATIVE

(75) Inventors: Noboru Murakami, Miyazaki (JP); Keiko Nakahara, Miyazaki (JP); Kenji Kangawa, Osaka (JP)

(73) Assignees: UNIVERSITY OF MIYAZAKI, Miyazaki-shi, Miyazaki (JP); NATIONAL CEREBRAL AND CARDIOVASCULAR CENTER, Suita-shi, Osaka (JP); DAIICHI SANKYO COMPANY, LIMITED, Tokyo (JP)

(*) Notice: Subject to any disclaimer, the term of this patent is extended or adjusted under 35 U.S.C. 154(b) by 132 days.

(21) Appl. No.: 14/002,570

(22) PCT Filed: Sep. 2, 2011

(86) PCT No.: PCT/JP2011/070077
§ 371 (c)(1),
(2), (4) Date: Nov. 8, 2013

(87) PCT Pub. No.: WO2012/117592
PCT Pub. Date: Sep. 7, 2012

(65) Prior Publication Data
US 2015/0238570 A1 Aug. 27, 2015

(30) Foreign Application Priority Data
Mar. 3, 2011 (JP) ................. 2011-047025

(51) Int. Cl.
*A61K 38/18* (2006.01)
*A61K 38/22* (2006.01)
(52) U.S. Cl.
CPC ..................... *A61K 38/22* (2013.01)
(58) Field of Classification Search
None
See application file for complete search history.

(56) References Cited

U.S. PATENT DOCUMENTS

| 2009/0170763 A1 | 7/2009 | Kangawa et al. |
| 2009/0305969 A1 | 12/2009 | Murakami et al. |

FOREIGN PATENT DOCUMENTS

| EP | 2070549 A1 | 6/2009 |
| JP | 2009-79937 A | 4/2009 |
| WO | WO-01/07475 A1 | 2/2001 |
| WO | WO-2005039625 A1 | 5/2005 |
| WO | WO-2007/058360 A1 | 5/2007 |
| WO | WO-2008/018597 A1 | 2/2008 |

OTHER PUBLICATIONS

Kheradmand et al. (Regulatory Peptides, 167: 97-104, 2011).*

H. Ariyasu et al., "Transgenic Mice Overexpressing Des-Acyl Ghrelin Show Small Phenotype", Endocrinology, 2005, vol. 146, No. 1, pp. 355-364.
A. Asakawa et al., "Stomach regulates energy balance via acylated ghrelin and desacyl ghrelin", GUT, 2005, vol. 54, No. 1, pp. 18-24.
G. Baldanzi et al., "Ghrelin and des-acyl ghrelin inhibit cell death in cardiomyocytes and endothelial cells through ERK1/2 and PI 3-kinase/AKT", The Journal of Cell Biology, Dec. 23, 2002, vol. 159, No. 6, pp. 1029-1037.
P. Cassoni et al., "Expression of ghrelin and biological activity of specific receptors for ghrelin and des-acyl ghrelin in human prostate neoplasms and related cell lines", European Journal of Endocrinology, 2004, vol. 150, pp. 173-184.
A. Howard et al., "A Receptor in Pituitary and Hypothalamus That Functions in Growth Hormone Release", Science, Aug. 16, 1996, vol. 273, pp. 974-977.
M. Kojima et al., "Ghrelin is a growth-hormone-releasing acylated peptide from stomach", Letters to Nature, Dec. 9, 1999, vol. 402, pp. 656-660.
M. Korbonits et al., "Ghrelin-a hormone with multiple functions", Frontiers in Neuroendocrinology, 2004, vol. 25, pp. 27-68.
A. Lely et al., "Biological, Physiological, Pathophysiological, and Pharmacological Aspects of Ghrelin", Endocrine Reviews, 2004, vol. 25, No. 3, pp. 426-457.
K. Nakahara et al., "Maternal Ghrelin Plays an Important Role in Rat Fetal Development during Pregnancy", Endocrinology, 2006, vol. 147, No. 3, pp. 1333-1342.
M. Nakazato et al., "A role for ghrelin in the central regulation of feeding", Letters to Nature, Jan. 11, 2001, vol. 409, pp. 194-198.
S. Perboni et al., "Appetite and gastrointestinal motility: Role of ghrelin-family peptides", Clinical Nutrition, 2010, vol. 29, pp. 227-234.
T. Sato, "The Journal of Japan Foundation for Applied Enzymology", Feb. 1, 2011, No. 45, p. 107 (excerpt).
M. Shintani et al., "Ghrelin, an Endogenous Growth Hormone Secretagogue, is a Novel Orexigenic Peptide That Antagonizes Leptin Action Through the Activaton of Hypothalamic Neuropeptide Y/Y1 Receptor Pathway", Diabetes, Feb. 2001, vol. 50, pp. 227-232.
E. Vestergaard et al., "Acute Peripheral Metabolic Effects of Intraarterial Ghrelin Infusion in Healthy Young Men", J Clin Endocrinol Metab, Feb. 2011, vol. 96, No. 2, pp. 468-477.
A. Wren et al., "The Novel Hypothalamic Peptide Ghrelin Stimulates Food Intake and Growth Hormone Secretion", Endocrinology, 2000, vol. 141, No. 11, pp. 4325-4328.
W. Zhang et al., "Ghrelin stimulates neurogenesis in the dorsal motor nucleus of the vagus", J Physiol, 2004, vol. 559, No. 3, pp. 729-737.

(Continued)

*Primary Examiner* — Christine J Saoud
(74) *Attorney, Agent, or Firm* — Drinker Biddle & Reath LLP

(57) ABSTRACT

An object of the present invention is to provide a hypothermic agent for an animal, a therapeutic agent for hyperthermia in an animal, etc. The present invention provides a hypothermic agent for an animal, a therapeutic agent for hyperthermia in an animal, etc., the agents etc. comprising desacyl ghrelin or its derivative, or a pharmaceutically acceptable salt thereof as an active ingredient.

5 Claims, 3 Drawing Sheets

(56) References Cited

OTHER PUBLICATIONS

Yoshiyuki Inoue et al., "Actions of ghrelin and desacyl ghrelin on autonomic nervous system", Proceedings of 150th meeting of the Japanese Society of Veterinary Science (excerpt), http://tech.obihiro.ac.jp/~jsvs150/program/pdf/Syo_I.pdf, Sep. 3, 2010.

Yoshiyuki Inoue et al. "Actions of ghrelin and desacyl ghrelin on automatic nervous system", Proceedings of 150th meeting of the Japanese Society of Veterinary Science Summary of lecture, Sep. 8, 2010, Corresponding page: p. 307.

International Preliminary Report on Patentability mailed Sep. 3, 2013 in PCT/JP2011/070077 filed Sep. 2, 2011.

International Search Report mailed Oct. 25, 2011 in PCT/JP2011/070077 filed Sep. 2, 2011.

Hikaru Ito: Simultaneous Measurement of Temperature at Different Sites in Clinical Entities Displaying Hypothermia: The Autonomic Nervous System, 1990; 27:281-291, (with a partial translation thereof).

* cited by examiner

SEQUENCE LISTING

```
<160> NUMBER OF SEQ ID NOS: 18

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens

<400> SEQUENCE: 2

Gly Ser Ser Phe Leu Ser Pro Glu His Gln Arg Val Gln Arg Lys Glu
1               5                   10                  15
```

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Canis familiaris

<400> SEQUENCE: 3

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Canis familiaris

<400> SEQUENCE: 4

Gly Ser Ser Phe Leu Ser Pro Glu His Gln Lys Leu Gln Arg Lys Glu
1               5                   10                  15

Ser Lys Lys Pro Pro Ala Lys Leu Gln Pro Arg
            20                  25

<210> SEQ ID NO 5
<211> LENGTH: 27
<212> TYPE: PRT
<213> ORGANISM: Felis silvestris catus

<400> SEQUENCE: 5

Gly Ser Ser Phe Leu Ser Pro Glu His Gln Lys Val Gln Arg Lys Glu
1               5                   10                  15

Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus

<400> SEQUENCE: 7

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries

```
<400> SEQUENCE: 8

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Equus caballus

<400> SEQUENCE: 9

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 10
<211> LENGTH: 28
<212> TYPE: PRT
<213> ORGANISM: Macaca mulatta

<400> SEQUENCE: 10

Gly Ser Ser Phe Leu Ser Pro Glu His Gln Arg Ala Gln Gln Arg Lys
1               5                   10                  15

Glu Ser Lys Lys Pro Pro Ala Lys Leu Gln Pro Arg
            20                  25

<210> SEQ ID NO 11
<211> LENGTH: 27
<212> TYPE: PRT
<213> ORGANISM: Capra aegagrus hircus

<400> SEQUENCE: 11

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 12
<211> LENGTH: 28
<212> TYPE: PRT
<213> ORGANISM: Oryctolagus cuniculus

<400> SEQUENCE: 12

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 13
<211> LENGTH: 28
<212> TYPE: PRT
<213> ORGANISM: Mus musculus

<400> SEQUENCE: 13

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

```
<210> SEQ ID NO 14
<211> LENGTH: 28
<212> TYPE: PRT
<213> ORGANISM: Rattus norvegicus

<400> SEQUENCE: 14

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 15
<211> LENGTH: 27
<212> TYPE: PRT
<213> ORGANISM: Rattus norvegicus

<400> SEQUENCE: 15

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 16
<211> LENGTH: 24
<212> TYPE: PRT
<213> ORGANISM: Gallus domesticus

<400> SEQUENCE: 16

Gly Ser Ser Phe Leu Ser Pro Thr Tyr Lys Asn Ile Gln Gln Gln Lys
1               5                   10                  15

Gly Thr Arg Lys Pro Thr Ala Arg
            20

<210> SEQ ID NO 17
<211> LENGTH: 24
<212> TYPE: PRT
<213> ORGANISM: Gallus domesticus

<400> SEQUENCE: 17

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 18
<211> LENGTH: 26
<212> TYPE: PRT
<213> ORGANISM: Gallus domesticus

<400> SEQUENCE: 18

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25
```

METHODS OF LOWERING BODY TEMPERATURE BY ADMINISTRATION OF DESACYL GHRELIN OR ITS DERIVATIVE

CROSS REFERENCE TO RELATED APPLICATIONS

This application is a National Stage of International Application No. PCT/JP2011/070077, filed Sep. 2, 2011, and which claims benefit of Japanese Patent Application No.: 2011-047025 filed Mar. 3, 2011, both of which are incorporated by reference herein.

REFERENCE TO A SEQUENCE LISTING

A Sequence Listing containing SEQ ID NOS: 1-18 is incorporated herein by reference.

TECHNICAL FIELD

The present invention relates to a hypothermic agent for an animal and a therapeutic agent for hyperthermia in an animal. In particular, the present invention relates to a hypothermic agent and a therapeutic agent for hyperthermia, the agents comprising desacyl ghrelin or its derivative as an active ingredient, for use in lowering an increased body temperature of an animal suffering from heat illness etc. or in the suppression of an increase in the body temperature of an animal suffering from heat illness etc., thereby helping the animal to survive. The present invention also relates to a method for lowering the body temperature of an animal and a therapeutic method for hyperthermia in an animal, the methods comprising administering the above agent to an individual.

BACKGROUND ART

In recent years, in line with the global warming trend, the average temperature in Japan is steadily increasing, and the records of the highest temperature and the number of sultry nights (which are defined as the nights when the temperature does not fall below 25° C.) in summer are being broken every year. The temperature increase in summer is remarkable especially in cities. The incidence of heat illness in sports, manual labor, or daily life has been reported (Miyake et al., Nihon Kyukyu Igakukai Zasshi (Journal of Japanese Association for Acute Medicine), 19: 309-21 (2008)). Investigation on heat illness patients who were treated in emergency medical care centers across the country from June to August in 2006 revealed that the fatality rate is significantly high in patients with a body temperature of 40° C. or more. Heat illness with poor prognosis may lead to a very critical condition, which may result in death with multiple organ failure.

In order to prevent or counteract heat illness, the Ministry of Environment has issued Netchusho Kankyo Hoken Manual (the Environment Health Manual on Heat Illness).

There is also a report that the death toll due to heat illness is increasing not only in humans but also in livestock animals such as cattle, pigs, chickens (the Sankei Shimbun dated Sep. 3, 2010). During the period from July 1 to August 15 in 2010, the number of livestock animals that died or abandoned due to heat stroke etc. reached 959 dairy-cattle, 235 beef-cattle, 657 pigs, 289,000 broiler chickens and 136,000 egg-laying chickens (Kumamoto Prefecture Chuo-kaho News vol. 5, August (2010)). Minor health problems in livestock animals such as cattle, pigs, and chickens will affect their market values. If livestock animals died, the economic loss will reach several million yen per animal. In terms of companion animals such as dogs and cats, minor health problems in the animals will hugely affect the owners' daily lives. Thus health care of the above animals is a huge social problem.

In addition, the productivity and quality of livestock animals are known to deteriorate due to high air temperature and high humidity in summer. Under summer heat stress, reduction occurs in sperm production, egg maturation, fetal development, fetal growth, placenta maturation, etc., and also in the pregnancy rate (Nabenishi H. et al., J. Reprod. Dev. (2001) April 9, E. Pub.). Further, due to continuous high air temperature, reduction occurs in body weight gain, the amount of milk secretion, and the egg laying rate, and also in the milk quality (milk fat percentage) and the meat quality (Chikyu Ondanka Ni Taio shita Norin Suisan Kenkyu Kaihatsu Vision, p. 10 (March 2010, Agriculture, Forestry and Fishery Department, Yamagata Prefecture)). The reduction in the productivity of domestic fowls and livestock animals under summer heat is closely related to increase in the body temperature (Nonaka et al., Chikyukankyo (2009) 14: 215-222). Therefore, lowering the body temperature of livestock animals during the summer heat period is expected to improve the productivity of the livestock animals.

Animals have thermoregulatory functions such as perspiration and can maintain a constant body temperature regardless of changes in air temperature and weather. However, when high air temperature and high humidity conditions continue, or when the thermoregulatory functions are impaired, the body temperature of an animal may abnormally increase. In such cases, it is necessary to immediately notice the animal's unusual signs and treat the animal to lower the body temperature. In cases where increase in air temperature is predicted, lowering the body temperature of an animal in advance may be useful in maintaining good health of the animal. Further, even when the body temperature of an animal is already in the course of increasing, suppression of the increase enables early treatment and prevents the body temperature from reaching the lethal level. In particular, in the case of heat stroke, the body temperature of an animal sometimes reaches 40° C., which will increase the risk of death. Therefore, there has been a great demand for a means to prevent heat illness including heat stroke.

Ghrelin is a hormone discovered from the stomach in 1999 and is a peptide composed of an amino acid sequence consisting of 28 residues. The amino acid sequence has a very unique chemical structure in which the third amino acid from the N-terminus is acylated with a fatty acid (Non Patent Literature 1 and Patent Literature 1). Ghrelin is an endogenous brain-gut hormone that acts on the growth hormone secretagogue receptor 1a (GHS-R1a) (Non Patent Literature 2) and increases the secretion of growth hormone (GH) from the pituitary gland.

Ghrelin was initially isolated and purified from rats as an endogenous GHS-R ligand for GHS-R1a. Later, ghrelin amino acid sequences that are similar to the rat ghrelin in primary structure were found in vertebrates other than rats, for example, humans, mice, pigs, chickens, cattle, horses, sheep, dogs, cats, etc. (Patent Literature 1).

Desacyl ghrelin is a peptide generated through removal of the fatty acid from ghrelin. Desacyl ghrelin has almost no affinity to GHS-R1a and thus exhibits almost no activity to increase the secretion of growth hormone (GH) from the pituitary gland (Broglio, F. et al., J. Clin. Endocrinol. Metab., 89: 3062-5 (2004)). Desacyl ghrelin has also reported to exert an anorexigenic action (Perboni, S. & Inui, A., Clin. Nutr., 29: 227-34 (2010)). The actions of desacyl ghrelin are understood to be independent from GHS-R1a (Delhanty, P J. et al., PLoS One, 5: e11749 (2010)), but the receptors, physiological functions, etc. largely remain unknown.

Desacyl ghrelin, as with ghrelin, has also been reported to exert a cardioprotective activity through inhibition of apoptosis of cardiomyocytes (Non Patent Literature 3) and has been suggested to play a role in the fate of cells such as cell growth and cell death. Desacyl ghrelin also has been reported to exert an inhibitory action against the growth of prostate tumor cells (Non Patent Literature 4). Thus desacyl ghrelin is considered to act on receptors other than GHS-R1a. The reported effects of desacyl ghrelin on ingestive action include both enhancing and suppressing effects and overexpressed desacyl ghrelin results in a reduced level of IGF-1 and a small body size (Non Patent Literature 5).

Recent studies have also revealed that ghrelin increases appetite, that subcutaneous administration of ghrelin increases body weight and fat gain (Non Patent Literature 6, 7, and 8), and that ghrelin has the effect of improving the cardiac performance etc. (Non Patent Literature 9). Ghrelin also has GH secretion-promoting and appetite-increasing actions and hence has a potential to more effectively induce, through increasing appetite, GH's action of burning fat and converting it into energy or GH's anabolic action of increasing muscles (Non Patent Literature 10). Another potential of ghrelin to exert a hypothermic effect is disclosed in a patent application, although no Example is described for it (Patent Literature 2).

The inventors found that ghrelin and desacyl ghrelin exist in the amniotic fluid of pregnancy mother animals, investigated their functions and roles and, as a result, discovered that GHS-R1a exists in fetal skin cells and that desacyl ghrelin has a proliferative action for fetal skin cells (Non Patent Literature 11). As other desacyl ghrelin's actions, the effects on cancer cell growth etc. have been suggested (Non Patent Literature 12).

CITATION LIST

Patent Literature

Patent Literature 1: WO 01/07475 A1
Patent Literature 2: WO 2005/039625 A1

Non Patent Literature

Non Patent Literature 1:
Kojima et al., Nature, 402, pp. 656-660 (1999)
Non Patent Literature 2:
Howard et al., Science, 273, pp. 974-977 (1996)
Non Patent Literature 3:
Baldanzi et al., J. Cell Biol., 159, pp. 1029-1037 (2002)
Non Patent Literature 4:
Cassoni et al., Eur. J. Endocrinol., 150, pp. 173-184 (2004)
Non Patent Literature 5:
Ariyasu et al., Endocrinology, 146, pp. 355-364 (2005)
Non Patent Literature 6:
Wren et al., Endocrinology, 141, pp. 4325-4328 (2000)
Non Patent Literature 7:
Nakazato et al., Nature, 409, 194-198 (2001)
Non Patent Literature 8:
Shintani et al., Diabetes, 50, pp. 227-232 (2001)
Non Patent Literature 9:
Lely et al., Endocr. Rev., 25, pp. 656-660 (2004)
Non Patent Literature 10:
Korbonits et al., Front Neuroendocrinol., 25, pp. 27-68 (2004)
Non Patent Literature 11:
Nakahara et al., Endocrinology, 147, pp. 1333-42 (2006)
Non Patent Literature 12:
Zhang et al., J Physiol., 559, pp. 729-737 (2004)

SUMMARY OF INVENTION

Technical Problem

The present invention relates to a hypothermic agent for an animal and a therapeutic agent for hyperthermia in an animal, the agents comprising desacyl ghrelin or its derivative as an active ingredient. The present invention also relates to a method for lowering the body temperature of an animal and a therapeutic method for hyperthermia in an animal, the methods comprising administering the above agent to an individual.

Solution to Problem

The inventors found that the administration of an agent comprising desacyl ghrelin or its derivative, or a pharmaceutically acceptable salt thereof as an active ingredient to an animal (an individual) lowers the body temperature or suppresses an increase in the body temperature and that the agent can therefore be used for the treatment of an animal suffering from hyperthermia such as heat illness.

That is, the present invention relates to a hypothermic agent for an animal, the agent comprising desacyl ghrelin or its derivative, or a pharmaceutically acceptable salt thereof as an active ingredient.

The present invention also relates to a therapeutic agent for hyperthermia in an animal, the agent comprising desacyl ghrelin or its derivative, or a pharmaceutically acceptable salt thereof as an active ingredient.

The present invention also relates to a method for lowering the body temperature of an animal, the method comprising administering desacyl ghrelin or its derivative, or a pharmaceutically acceptable salt thereof to an individual.

The present invention also relates to a therapeutic method for hyperthermia in an animal, the method comprising administering desacyl ghrelin or its derivative, or a pharmaceutically acceptable salt thereof to an individual.

The present invention also relates to desacyl ghrelin or its derivative, or a pharmaceutically acceptable salt thereof for use in lowering the body temperature of an animal.

The present invention also relates to desacyl ghrelin or its derivative, or a pharmaceutically acceptable salt thereof for use in the treatment of hyperthermia in an animal.

The present invention also relates to use of desacyl ghrelin or its derivative, or a pharmaceutically acceptable salt thereof for the production of a hypothermic agent for an animal, the agent comprising desacyl ghrelin or its derivative, or a pharmaceutically acceptable salt thereof as an active ingredient.

The present invention also relates to use of desacyl ghrelin or its derivative, or a pharmaceutically acceptable salt thereof for the production of a therapeutic agent for hyperthermia in an animal, the agent comprising desacyl ghrelin or its derivative, or a pharmaceutically acceptable salt thereof as an active ingredient.

Therefore, the present invention more specifically relates to the following.

1) A hypothermic agent for an animal, the agent comprising desacyl ghrelin or its derivative, or a pharmaceutically acceptable salt thereof as an active ingredient.

2) The hypothermic agent according to the above 1), wherein the animal is selected from the group consisting of human, canine, feline, mouse, rat, rabbit, bovine, equine, porcine, ovine, and monkey.

3) The hypothermic agent according to the above 1) or 2), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

4) The hypothermic agent according to the above 3), wherein the basic amino acid is lysine or arginine.

5) The hypothermic agent according to any of the above 1) to 4), wherein the desacyl ghrelin or its derivative, or a pharmaceutically acceptable salt thereof as an active ingredient is contained in an amount of 0.001 mg to 1000 mg per dose unit.

6) A therapeutic agent for hyperthermia in an animal, the agent comprising desacyl ghrelin or its derivative, or a pharmaceutically acceptable salt thereof as an active ingredient.

7) The therapeutic agent for hyperthermia according to the above 6), wherein the animal is selected from the group consisting of human, canine, feline, mouse, rat, rabbit, bovine, equine, porcine, ovine, and monkey.

8) The therapeutic agent for hyperthermia according to the above 6) or 7), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

9) The therapeutic agent for hyperthermia according to the above 8), wherein the basic amino acid is lysine or arginine.

10) The therapeutic agent for hyperthermia according to any of the above 6) to 9), wherein the desacyl ghrelin or its derivative, or a pharmaceutically acceptable salt thereof as an active ingredient is contained in an amount of 0.001 mg to 1000 mg per dose unit.

11) A method for lowering the body temperature of an animal, the method comprising administering desacyl ghrelin or its derivative, or a pharmaceutically acceptable salt thereof to an individual.

12) The method for lowering the body temperature according to the above 11), wherein the animal is selected from the group consisting of human, canine, feline, mouse, rat, rabbit, bovine, equine, porcine, ovine, and monkey.

13) The method for lowering the body temperature according to the above 11) or 12), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

14) The method for lowering the body temperature according to the above 13), wherein the basic amino acid is lysine or arginine.

15) The method for lowering the body temperature according to any of the above 11) to 14), wherein the desacyl ghrelin or its derivative, or a pharmaceutically acceptable salt thereof is administered to an individual in an amount of 0.001 mg to 1000 mg per dose unit.

16) A therapeutic method for hyperthermia in an animal, the method comprising administering desacyl ghrelin or its derivative, or a pharmaceutically acceptable salt thereof to an individual.

17) The therapeutic method for hyperthermia according to the above 16), wherein the animal is selected from the group consisting of human, canine, feline, mouse, rat, rabbit, bovine, equine, porcine, ovine, and monkey.

18) The therapeutic method for hyperthermia according to the above 16) or 17), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

19) The therapeutic method for hyperthermia according to the above 18), wherein the basic amino acid is lysine or arginine.

20) The therapeutic method for hyperthermia according to any of the above 16) to 19), wherein the desacyl ghrelin or its derivative, or a pharmaceutically acceptable salt thereof as an active ingredient is administered to an individual in an amount of 0.001 mg to 1000 mg per dose unit.

21) Desacyl ghrelin or its derivative, or a pharmaceutically acceptable salt thereof for use in lowering the body temperature of an animal.

22) The desacyl ghrelin or its derivative, or a pharmaceutically acceptable salt thereof according to the above 21), wherein the animal is selected from the group consisting of human, canine, feline, mouse, rat, rabbit, bovine, equine, porcine, ovine, and monkey.

23) The desacyl ghrelin or its derivative, or a pharmaceutically acceptable salt thereof according to the above 21) or 22), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

24) The desacyl ghrelin or its derivative, or a pharmaceutically acceptable salt thereof according to the above 23), wherein the basic amino acid is lysine or arginine.

25) The desacyl ghrelin or its derivative, or a pharmaceutically acceptable salt thereof according to any of the above 21) to 24) for use in lowering the body temperature of an animal by administration to an individual in an amount of 0.001 mg to 1000 mg per dose unit.

26) Desacyl ghrelin or its derivative, or a pharmaceutically acceptable salt thereof for use in the treatment of hyperthermia in an animal.

27) The desacyl ghrelin or its derivative, or a pharmaceutically acceptable salt thereof according to the above 26), wherein the animal is selected from the group consisting of human, canine, feline, mouse, rat, rabbit, bovine, equine, porcine, ovine, and monkey.

28) The desacyl ghrelin or its derivative, or a pharmaceutically acceptable salt thereof according to the above 26) or 27), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

29) The desacyl ghrelin or its derivative, or a pharmaceutically acceptable salt thereof according to the above 28), wherein the basic amino acid is lysine or arginine.

30) The desacyl ghrelin or its derivative, or a pharmaceutically acceptable salt thereof according to any of the above 26) to 29) for use in the treatment of hyperthermia in an animal by administration to an individual in an amount of 0.001 mg to 1000 mg per dose unit.

31) Use of desacyl ghrelin or its derivative, or a pharmaceutically acceptable salt thereof for the production of a hypothermic agent for an animal, the agent comprising desacyl ghrelin or its derivative, or a pharmaceutically acceptable salt thereof as an active ingredient.

32) The use according to the above 31), wherein the animal is selected from the group consisting of human, canine, feline, mouse, rat, rabbit, bovine, equine, porcine, ovine, and monkey.

33) The use according to the above 31) or 32), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

34) The use according to the above 33), wherein the basic amino acid is lysine or arginine.

35) The use according to any of the above 31) to 34), wherein the hypothermic agent for an animal comprises the desacyl ghrelin or its derivative, or a pharmaceutically acceptable salt thereof as an active ingredient in an amount of 0.001 mg to 1000 mg per dose unit.

36) Use of desacyl ghrelin or its derivative, or a pharmaceutically acceptable salt thereof for the production of a therapeutic agent for hyperthermia in an animal, the agent comprising desacyl ghrelin or its derivative, or a pharmaceutically acceptable salt thereof as an active ingredient.

37) The use according to the above 36), wherein the animal is selected from the group consisting of human, canine, feline, mouse, rat, rabbit, bovine, equine, porcine, ovine, and monkey.

38) The use according to the above 36) or 37), wherein the desacyl ghrelin or its derivative is selected from the group consisting of
(1) a peptide having an amino acid sequence of any of SEQ ID NOs: 1 to 18,
(2) a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition,
(3) a peptide of (2) in which one or two basic amino acids are added to the C-terminus, and
(4) a peptide of (2) or (3) in which the C-terminus of the amino acid sequence is amidated.

39) The use according to the above 38), wherein the basic amino acid is lysine or arginine.

40) The use according to any of the above 36) to 39), wherein the therapeutic agent for hyperthermia in an animal comprises the desacyl ghrelin or its derivative, or a pharmaceutically acceptable salt thereof as an active ingredient in an amount of 0.001 mg to 1000 mg per dose unit.

The term "dose unit" herein means an amount of an agent that is administered at a time.

Advantageous Effects of Invention

An agent of the present invention comprising, as an active ingredient, desacyl ghrelin or its derivative, or a pharmaceutically acceptable salt thereof can be administered to various animals to exert a hypothermic effect on the animals. The agent also can be used for the treatment of an animal that has already developed hyperthermia such as heat illness. Further, the agent can be administered in advance to an animal to lower the body temperature of the animal, thereby preventing the animal from developing hyperthermia.

DESCRIPTION OF EMBODIMENTS

Figure 1:
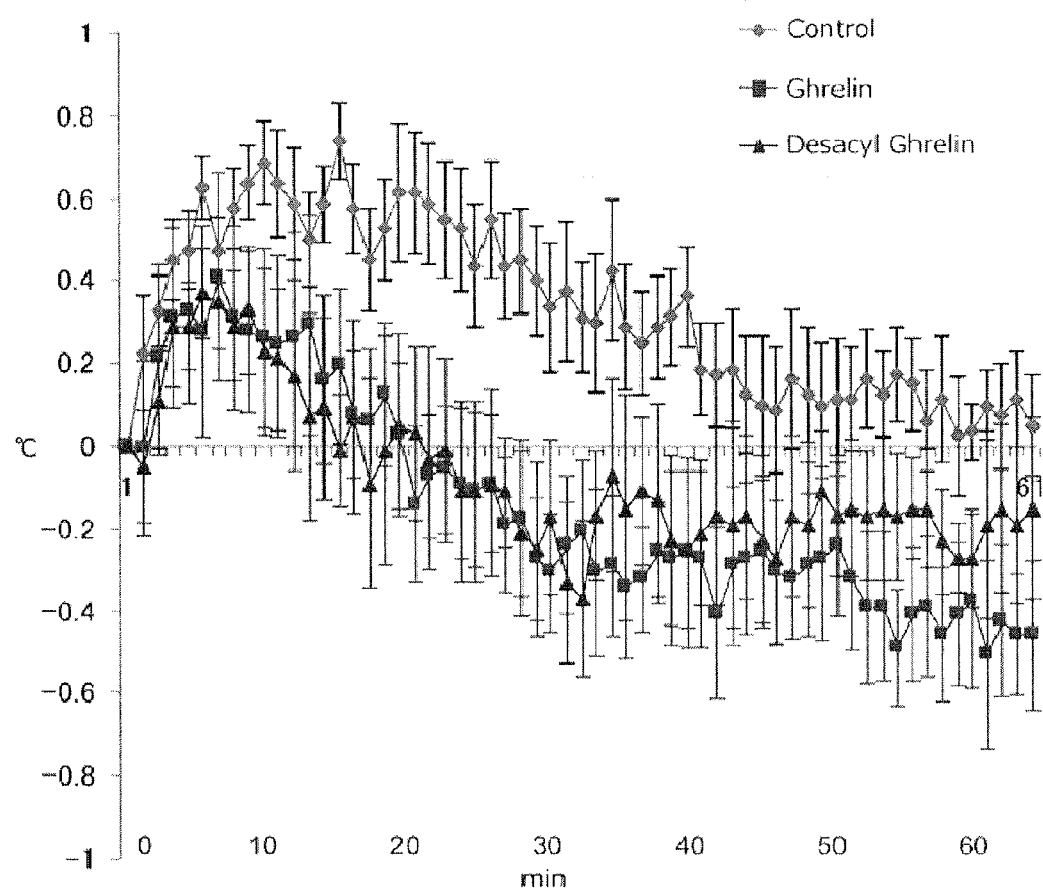
FIG. 1 is a chart showing the hypothermic effect of desacyl ghrelin that is intraperitoneally administered to rats with the normal body temperature. The triangle symbol represents the administration of desacyl ghrelin, the square symbol represents the administration of ghrelin, and the diamond symbol represents the administration of physiological saline. The vertical axis represents the changes in the back surface body temperature (° C.) of the rats and the horizontal axis represents the elapsed time (minutes) after injection. The back surface temperature at the time of injection (zero minutes) is 37.6 to 39.2° C.

The body temperature of an animal can be measured with a known method. For the measurement of the body temperature of an animal, the core body temperature maybe measured, or the surface body temperature maybe measured. Examples of the measurement method of the core body temperature include a measurement of the rectal temperature with a thermometer, etc. Examples of the measurement method of the surface body temperature include a method in which a thermometer is made into contact with a fixed point of the body surface of an animal, a method using thermography, etc. By the measurement method using thermography, the surface body temperature of any given sites such as dorsal and tail surfaces can be measured.

The core body temperature refers to the temperature inside the body, measured at the rectum etc. of an animal and the surface body temperature refers to the temperature of the surface of the body, measured at the skin surface of an animal.

The animal to be subjected to the administration of the hypothermic agent or the therapeutic agent for hyperthermia of the present invention is not particularly limited as long as it is a vertebrate. Examples of the subject animal include various kinds of animals, for example, human; mammals other than human such as porcine and bovine; birds such as chicken; etc. Among these, preferred are animals which are active mainly in the open air and thus of which body temperature is under the influence of a sudden change of the air temperature, etc. and examples thereof include human, canine, feline, rabbit, bovine, equine, porcine, ovine, monkey, etc. Particularly preferred are canine, feline, bovine, equine, porcine, and ovine.

The body temperature of an animal to be subjected to the administration of the hypothermic agent or the therapeutic agent for hyperthermia of the present invention may be a normal body temperature, or may be a higher than the normal body temperature.

The normal body temperature refers to a body temperature that is maintained in a constant range by the thermoregulatory function of an animal. The normal body temperature varies with the measurement site, the period of time at which the measurement is performed, etc., but is kept in a constant range which depends on the kinds of animals. For example, the normal body temperature of rats is 37 to 38° C. (core body temperature), the normal body temperature of humans is 34 to 37° C. (surface body temperature), the normal body temperature of felines is 38.1 to 39.2° C. (core body temperature), the normal body temperature of bovines (meat cattle) is 36.7 to 39.1° C. (core body temperature), the normal body temperature of bovines (dairy cows) is 38.0 to 39.3° C. (core body temperature), the normal body temperature of canines is 37.9 to 39.9° C. (core body temperature), the normal body temperature of goats is 38.5 to 39.7° C. (core body temperature), the normal body temperature of equines is 37.2 to 38.2° C. (core body temperature), the normal body temperature of porcines is 38.7 to 39.8° C. (core body temperature), and the normal body temperature of ovines is 38.5 to 39.9° C. (core body temperature).

For example, when animals are exposed to summer heat stress but the body temperature has not yet reached an abnormally high level, treatment may be provided to prevent hyperthermia. The symptoms that indicate exposure to summer heat stress are, for example in the case of dairy cows, a high rate of respiration, longer hours of standing, drooling, etc. (Chikusan Club 21, No. 73, April, 2011).

In addition, reduction in the conception rate in artificial insemination (AI) is regarded as a serious problem not only in Japan but also in foreign countries (Chikusan Club 21, No. 74, June, 2011). Reducing the body temperature of animals in summer, when the pregnancy rate decreases, may improve the pregnancy rate.

Hyperthermia refers to a condition in which dysfunction of thermoregulation occurs and the core body temperature, which is normally regulated by homeostasis, becomes higher than the normal level. Hyperthermia may be caused by external environmental conditions and also may be secondarily caused by internal heat production (Resuscitation (2005) 6751, 5135-170). Hyperthermia due to environmental conditions is developed when a body absorbs more heat (usually in a form of radiant heat) than that dissipated by the thermoregulatory function. Hyperthermia is a series of diseases related to heat, which start with heat stress, progresses to heat exhaustion and heat stroke, and may result in multiple organ failure or cardiac arrest (Bouchama A, Knochel J P., New England Journal of Medicine; 346: 1978-88 (2002)).

A body temperature of an animal higher than the normal body temperature damages various organs such as the brain, nerves, internal organs, motor organs, etc. The symptoms of hyperthermia include, for example, cramp, fainting, dizziness, fatigue, collapse, headache, nausea, vomiting, delirium, coma, body temperature increase, etc. Among the diseases included in hyperthermia, heat stroke and sunstroke, which are severe cases of heat illness, and anesthesia-related hyperthermia are critical clinical conditions with very high mortality rates. Persistence of hyperthermia over a certain period of time may cause blood coagulation, multiple organ failure, etc., which may lead an animal to death.

Hyperthermia is developed, for example, when an animal is left in a summer heat environment with, for example, high air temperature and high humidity and excessive heat not sufficiently released through perspiration accumulates in the body, or when the body temperature abnormally increases during or after surgery.

The conditions in which an animal develops hyperthermia are various depending on the animal concerned. For example, an animal may develop hyperthermia if left outside at an air temperature higher than the body temperature by 5° C. or more in a humidity exceeding 70% for 30 minutes or longer. A human may develop hyperthermia if left in an environment with, for example, an air temperature of 28° C. or more and a humidity of 75% or more. A rat may develop hyperthermia if left in an environment with, for example, an air temperature of 33° C. or more and a humidity of 60% or more for 30 minutes or longer.

The substances that can be used in the present invention may include, for example, desacyl ghrelin and a substance having a binding activity to a desacyl ghrelin binding site. Whether a substance has the activity of desacyl ghrelin can be determined through investigation on the binding activity to a desacyl ghrelin binding site with the use of a labeled desacyl ghrelin. That is, whether a substance "has the activity of replacing a labeled desacyl ghrelin" can be easily determined by allowing a test substance to act on a desacyl ghrelin binding site present on rat fetal spinal cord cells and measuring the radioactivity of the remaining labeled desacyl ghrelin by a simple known method. For example, the determination can be performed by radioreceptor assay using γ-spectrophotometer in which the radioactivity of $^{125}$I-labeled desacyl ghrelin bound to the binding sites in a solution not containing desacyl ghrelin is measured and replacement of the $^{125}$I-labeled desacyl ghrelin with desacyl ghrelin is detected as the reduction in the radioactivity at the binding sites. Alternatively, for example, the determination can be performed by a method in which a solubilized fraction of the cell membrane of rat fetal spinal cord cells is incubated with $^{125}$I-labeled desacyl ghrelin to allow binding and subjected to evaluation by radiography after electrophoresis. Further alternatively, the determination can be performed by administering a test substance to rats placed under conditions of room temperature or of high air temperature and high humidity and measuring changes in the body temperature.

A particularly preferred substance that can be used in the present invention is desacyl ghrelin or its derivative, or a pharmaceutically acceptable salt thereof.

The term "desacyl ghrelin" herein refers to desacyl ghrelin derived from various kinds of animals. Preferred is desacyl ghrelin derived from animals such as human, canine, feline, porcine, bovine, ovine, equine, monkey, goat, rabbit, mouse, rat, chicken, etc. Particular preferred is a peptide having a sequence of any of SEQ ID NOs: 1 to 18, which are shown below.

```
Human:
                                        (SEQ ID NO: 1)
GSSFLSPEHQRVQQRKESKKPPAKLQPR (SEQ ID NO: 2)
GSSFLSPEHQRVQ-RKESKKPPAKLQPR Canine:
                                        (SEQ ID NO: 3)
GSSFLSPEHQKLQQRKESKKPPAKLQPR (SEQ ID NO: 4)
GSSFLSPEHQKLQRKESKKPPAKLQPR Feline:
                                        (SEQ ID NO: 5)
GSSFLSPEHQKVQRKESKKPPAKLQPR Porcine:
                                        (SEQ ID NO: 6)
GSSFLSPEHQKVQQRKESKKPAAKLKPR Bovine:
                                        (SEQ ID NO: 7)
GSSFLSPEHQKLQRKEAKKPSGRLKPR Ovine:
                                        (SEQ ID NO: 8)
GSSFLSPEHQKLQRKEPKKPSGRLKPR Equine:
                                        (SEQ ID NO: 9)
GSSFLSPEHHKVQHRKESKKPPAKLKPR Monkey:
                                        (SEQ ID NO: 10)
GSSFLSPEHQRAQQRKESKKPPAKLQPR Goat:
                                        (SEQ ID NO: 11)
GSSFLSPEHQKLQ-RKEPKKPSGRLKPR Rabbit:
                                        (SEQ ID NO: 12)
GSSFLSPEHQKVQQRKESKKPAAKLKPR Mouse:
                                        (SEQ ID NO: 13)
GSSFLSPEHQKAQQRKESKKPPAKLQPR Rat:
                                        (SEQ ID NO: 14)
GSSFLSPEHQKAQQRKESKKPPAKLQPR (SEQ ID NO: 15)
GSSFLSPEHQKAQRKESKKPPAKLQPR Chicken:
                                        (SEQ ID NO: 16)
GSSFLSPTYKNIQQQKGTRKPTAR (SEQ ID NO: 17)
GSSFLSPTYKNIQQQKDTRKPTAR (SEQ ID NO: 18)
GSSFLSPTYKNIQQQKDTRKPTARLH
```

(In the above sequences, amino acid residues are represented by the one-letter code.)

The "desacyl ghrelin derivative" herein includes, for example, (1) a desacyl ghrelin derivative which is a peptide having an amino acid sequence of any of SEQ ID NOs: 1 to 18 in which the sequence of the N-terminus to the fourth amino acid is retained at the N-terminal side and one to several amino acids in the sequence of the fifth amino acid to the C-terminus are subjected to deletion, substitution and/or addition, (2) a desacyl ghrelin derivative which is a peptide of (1) in which one or two basic amino acids are added to the C-terminus, and (3) a desacyl ghrelin derivative which is a peptide of (1) or (2) in which the C-terminus of the amino acid sequence is amidated.

Other desacyl ghrelin derivatives can be easily designed in accordance with, for example, Patent Literature 1 mentioned above.

The number of the amino acids that are deleted etc. in "a peptide having an amino acid sequence in which one to several amino acids are subjected to deletion, substitution and/or addition" may be any number as long as it is not more than the number obtained by subtracting 4 from the number of the amino acids constituting the amino acid sequence of any of SEQ ID NOs: 1 to 18. That is, the number of the amino acids that are deleted etc. is not particularly limited as long as the sequence of the N-terminus to the fourth amino acid is retained in the above peptides. Preferably, 1, 2, 3, 4, 5, 6, 7, 8, 9, 10, 11, 12, 13, 14, 15, 16, 17, 18, 19, 20, 21, 22, 23, or 24 amino acids can be subjected to deletion, substitution and/or addition.

For example, in the case of a peptide having the amino acid sequence of SEQ ID NO: 16 or 17 (chicken), among the 24 amino acids constituting the amino acid sequence, 1 to 20 amino acids excluding the 4 amino acids constituting the sequence of the N-terminus to the fourth amino acid can be subjected to deletion, substitution and/or addition.

As long as the substitution is from amino acids to other amino acids having similar properties (electric charge and/or polarity), the substitution of many amino acids does not result in the loss of a desired function.

The above basic amino acid may be, for example, asparagine, glutamine, lysine, arginine, ornithine, etc. and among these preferred is lysine or arginine.

For administration to an individual animal, desacyl ghrelin derived from the same animal species as that to be subjected to the administration may be used, or desacyl ghrelin derived from a different animal species from that to be subjected to the administration may be used. Preferably, desacyl ghrelin derived from the same animal species as that to be subjected to the administration is used. For example, a feline-derived desacyl ghrelin (a peptide having an amino acid sequence of SEQ ID NO: 5 or a pharmaceutically acceptable salt thereof) can be administered to a canine, but preferably a canine-derived desacyl ghrelin (a peptide having an amino acid sequence of SEQ ID NO: 3 or 4, or a pharmaceutically acceptable salt thereof) is administered to a canine.

The desacyl ghrelin or its derivative of the present invention can be prepared by a conventional method (for example, see J. Med. Chem., 43, pp. 4370-4376, 2000 and Patent Literature 1). For example, the desacyl ghrelin or its derivative can be isolated from natural raw materials, or produced by recombinant DNA technology and/or chemical synthesis. For example, in the production method using recombinant DNA technology, the peptide compound of the present invention can be obtained by culturing a host cell transformed with an expression vector having the DNA encoding the peptide compound of the present invention and recovering the peptide of interest from the culture.

Examples of the vector for inserting the gene include *Escherichia coli* vectors (pBR322, pUC18, pUC19, etc.), *Bacillus subtilis* vectors (pUB110, pTP5, pC194, etc.), yeast vectors (a YEp type, a YRp type, a YIp type), animal cell vectors (a retrovirus, a vaccinia virus, etc.), etc. Any other vectors can also be used as long as they can stably carry the gene of interest into a host cell. The vectors are introduced into appropriate host cells. The method for inserting the gene of interest into a plasmid or introducing it into a host cell may be a method described in, for example, Molecular Cloning (Sambrook et al., 1989).

For the expression of the peptide gene of interest in the above plasmid, a promoter is connected to the upstream of the gene in order to function.

The promoter used in the present invention may be any promoter as long as it is suitable for the host cell used to express the gene of interest. For example, when the host cell to be transformed is the genus *Escherichia*, a lac promoter, a trp promoter, a lpp promoter, a λPL promoter, a recA promoter, etc. can be used; when the host cell is the genus *Bacillus*, a SPO1 promoter, a SPO2 promoter, etc. can be used; when the host cell is a yeast, a GAP promoter, a PHO5 promoter, an ADH promoter, etc. can be used; and when the host cell is an animal cell, an SV40-derived promoter, a retrovirus-derived promoter, etc. can be used.

The vector carrying the gene of interest obtained as above is used to transform the host cell. The host cells that can be used are bacteria cells (e.g., the genus *Escherichia*, the genus *Bacillus*, etc.), yeast cells (the genus *Saccharomyces*, the genus *Pichia*, the genus *Candida*, etc.), animal cells (CHO cells, COS cells, etc.), etc. A suitable medium for culture is a liquid medium and the medium particularly preferably contains a carbon source, a nitrogen source, etc. that are necessary for the growth of the transformed cells to be cultured. If desired, a vitamin, a growth-promoting factor, a serum, etc. can be added to the medium.

After culture, the peptide of the present invention is separated from the culture and purified by a conventional method. For example, the substance of interest is extracted from the cultured bacteria or cells by recovering the bacteria and cells after culture, suspending them into a buffer solution containing a protein denaturing agent (guanidine hydrochloride etc.), disrupting the bacteria or cells by ultrasonication etc., and centrifuging the bacteria or cells. Next, purification of the substance of interest from the supernatant can be performed in accordance with the molecular weight, solubility, electric charge (isoelectric point), affinity, etc. of the substance of interest, by any of various separation and purification methods such as gel filtration, ultrafiltration, dialysis, SDS-PAGE, and various types of chromatography, appropriately combined as needed.

The desacyl ghrelin or its derivative of the present invention can be chemically synthesized by a conventional method. For example, the desacyl ghrelin or its derivative can be prepared by condensing amino acids having protecting groups by a liquid-phase method and/or solid phase method, extending the peptide chain, removing all the protecting groups with an acid, and purifying the obtained crude product by the above purification method.

Various production methods of peptides are conventionally known. The peptide of the present invention can also be easily produced by a known method, for example, a classical peptide synthesis method or a solid phase method.

A salt of the desacyl ghrelin or of a desacyl ghrelin derivative that can be used in the present invention is preferably a pharmaceutically acceptable salt. Examples thereof include a salt with an inorganic base, a salt with an organic base, a salt with an inorganic acid, a salt with an organic acid, a salt with a basic or acidic amino acid, etc.

Preferred examples of the salt with an inorganic base include alkali metal salts such as a sodium salt and a potassium salt; alkaline earth metal salts such as a calcium salt and a magnesium salt; an aluminum salt; an ammonium salt; etc.

Preferred examples of the salt with an organic base include a salt with trimethylamine, triethylamine, pyridine, picoline, ethanolamine, diethanolamine, triethanolamine, dicyclohexylamine, N,N'-dibenzylethylenediamine, etc.

Preferred examples of the salt with an inorganic acid include a salt with hydrochloric acid, hydrobromic acid, nitric acid, sulfuric acid, phosphoric acid, etc.

Preferred examples of the salt with an organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salt with a basic amino acid include a salt with arginine, lysine, ornithine, etc. Preferred examples of the salt with an acidic amino acid include a salt with aspartic acid, glutamic acid, etc.

Among the above salts, most preferred are a sodium salt and a potassium salt.

The agent of the present invention comprising desacyl ghrelin or its derivative, or a pharmacologically acceptable salt thereof as an active ingredient can be obtained by subjecting the active ingredient to mixing etc. with a pharmacologically acceptable carrier, an excipient, a filler, etc. and then used for an individual (e.g., human, canine, feline, mouse, rat, rabbit, bovine, equine, porcine, ovine, monkey, etc.).

Examples of the pharmaceutically acceptable carrier include various organic or inorganic carrier substances that are commonly used as materials for pharmaceutical formulations. Such a carrier is blended as an excipient, a lubricant, a binder, or a disintegrant for solid formulations; or as a solvent, a solubilizing agent, a suspending agent, an isotonic agent, a buffering agent, or a soothing agent for liquid formulations; etc.

If needed, additives for pharmaceutical formulations, such as a preservative, an antioxidant, a colorant, and a sweetener can also be used.

Preferred examples of the excipient include lactose, saccharose, D-mannitol, starch, crystalline cellulose, light anhydrous silicic acid, etc.

Preferred examples of the lubricant include magnesium stearate, calcium stearate, talc, colloidal silica, etc.

Preferred examples of the binder include crystalline cellulose, saccharose, D-mannitol, dextrin, hydroxypropyl cellulose, hydroxypropyl methylcellulose, polyvinylpyrrolidone, etc.

Preferred examples of the disintegrant include starch, carboxymethyl cellulose, carboxymethyl cellulose calcium, croscarmellose sodium, carboxymethyl starch sodium, etc.

Preferred examples of the solvent include water for injection, alcohol, propylene glycol, macrogol, sesame oil, corn oil, etc.

Preferred examples of the solubilizing agent include polyethylene glycol, propylene glycol, D-mannitol, benzyl benzoate, ethanol, trisaminomethane, cholesterol, triethanolamine, sodium carbonate, sodium citrate, etc.

Preferred examples of the suspending agent include surfactants such as stearyltriethanolamine, sodium lauryl sulfate, lauryl aminopropionic acid, lecithin, benzalkonium chloride, benzethonium chloride, and glyceryl monostearate; hydrophilic polymers such as polyvinyl alcohol, polyvinylpyrrolidone, carboxymethyl cellulose sodium, methylcellulose, hydroxymethylcellulose, hydroxyethyl cellulose, and hydroxypropyl cellulose; etc.

Preferred examples of the isotonic agent include sodium chloride, glycerin, D-mannitol, etc.

Preferred examples of the buffering agent include buffer solutions containing a buffering agent such as a phosphate, an acetate, a carbonate, and a citrate, etc.

Preferred examples of the soothing agent include benzyl alcohol etc.

Preferred examples of the preservative include p-hydroxybenzoate esters, chlorobutanol, benzyl alcohol, phenethyl alcohol, dehydroacetic acid, sorbic acid, etc.

Preferred examples of the antioxidant include a sulfite, ascorbic acid, etc.

The administration method of the agent of the present invention is not particularly limited. Examples of parenteral administration methods for an individual animal include intravenous, subcutaneous, intramuscular or intraperitoneal injection, nasal administration, transpulmonary administration, suppository administration, eye drop administration, etc. Among these, preferred is intravenous, intraperitoneal, subcutaneous, or intramuscular injection in view of immediate exertion of the hypothermic effect. Examples of oral administration methods for an individual animal include oral administration of a liquid preparation, dietary administration, etc.

The dosage of the agent is not particularly limited in the present invention and can be appropriately selected depending on the purpose of use, the age, weight, species, symptoms, conditions of an individual to be subjected to the administration, a concomitant drug, etc. When a single dose or multiple doses are administered to an adult individual, the desacyl ghrelin or its derivative, or a pharmaceutically acceptable salt as an active ingredient is administered preferably in an amount of 0.001 mg to 1000 mg per dose, more preferably in an amount of 0.01 mg to 100 mg per dose.

The administration of the agent is performed so that a predetermined amount of the agent is administered to an animal. The predetermined amount may be administered in a single dose or multiple doses.

The administration of the agent may be single-dose administration or multiple-dose administration. In the case of multiple-dose administration, the agent may be administered once to several times per day for one day to one week. Preferably, the agent is administered twice or three times per day for about one day to three days.

The timing of administration of the agent is not particularly limited. Since the agent exerts the hypothermic effect 10 to 60 minutes after administration to an animal, administration is preferably performed at the time of the need for lowering the body temperature or immediately before the need arises.

The agent of the present invention exerts a superior hypothermic effect compared with other agents comprising ghrelin as an active ingredient. That is, the agent of the present invention can be used to immediately lower the body temperature of an animal suffering from the symptoms (such as hyperthermia etc.) that threaten the animal's life. The agent of the present invention can also be used to lower the body temperature of an animal (such as livestock animals etc.) as needed during the summer heat period.

The administration of the agent of the present invention to an animal increases the peripheral body temperature of the animal, which indicates that the agent promotes heat dissipation from the body. That is, the agent acts on the peripheral or central nervous systems and activates the radiation of heat from the periphery of the animal body, thereby efficiently exhausting heat from the body. Thus, the agent can exert the hypothermic effect on an animal.

The formulation type of the agent of the present invention is preferably a formulation suitable for oral administration. Examples of the formulation suitable for oral administration include a syrup, a tablet, a capsule, etc.

In addition, the formulation type of the agent of the present invention is preferably a formulation suitable for parenteral administration. Examples of the formulation suitable for parenteral administration include an intravenous, intracutaneous, subcutaneous, or intramuscular injection, an intravenous fluid, a suppository, an eye drop, a transdermal absorption formulation, a transmucosal absorption formulation, an inhalant, etc. Among these formulation types, preferred is the above injection. Particularly when the individual is a companion animal such as a canine and a feline under home treatment, preferred formulation types are a transmucosal absorption formulation, an inhalant, a suppository, an eye drop, etc. These formulation types are known to a person skilled in the art and therefore a person skilled in the art can appropriately select a formulation type suitable for a desired route of administration and formulate the agent into a pharmaceutical composition or a therapeutic agent using if needed one or more additives usable in the art.

For example, the agent in the form of an injection, an intravenous fluid, or an eye drop can be prepared and provided by dissolving desacyl ghrelin or a substance that acts on a desacyl ghrelin binding site as an active ingredient together with one or more additives for formulation such as an appropriate buffer solution, a sugar solution, an isotonic agent, a pH adjusting agent, a soothing agent, and a preservative in distilled water for injection, subjecting the solution to sterile filtration (with a filter), and placing the filtrate in an ampoule or vial, or freeze-drying the obtained filtrate to give a freeze-dried formulation. Examples of the additives include sugars such as glucose, mannitol, xylitol, and lactose; hydrophilic polymers such as polyethylene glycol; alcohols such as glycerol; amino acids such as glycine; proteins such as serum albumin; salts such as NaCl and sodium citrate; acids such as acetic acid, tartaric acid, and ascorbic acid; surfactants such as Tween 80; reducing agents such as sodium sulfite; etc. Such a formulation can be used as an injection or an intravenous fluid by dissolving with water for injection or physiological saline at the time of use. For transmucosal administration, intranasally administered formulations (nasally administered formulations) such as a nasal drop and an intranasal spray are suitable, and for transpulmonary administration, an inhalant etc. are suitable.

The amount of the desacyl ghrelin or its derivative, a pharmaceutically acceptable salt thereof per formulation is preferably 0.001 mg to 1000 mg, more preferably 0.01 mg to 100 mg. The agent of the present invention comprises the desacyl ghrelin or its derivative, or a pharmaceutically acceptable salt thereof as an active ingredient preferably in an amount of 0.001 mg to 100 mg, more preferably 0.01 mg to 10 mg per dose unit. Preferably, the formulation is administered once to several times a day.

EXAMPLES

The present invention will be specifically illustrated below with reference to Examples, but the present invention is not limited thereto.

Example 1

Hypothermic Effect of Desacyl Ghrelin in Rats with Normal Body Temperature

In this Example, a rat-derived desacyl ghrelin (SEQ ID NO: 14) was used as desacyl ghrelin. The rat-derived desacyl ghrelin (chemically synthesized by Peptide Institute, Inc.) was purchased and a rat-derived desacyl ghrelin for administration was prepared so that 0.1 mg of the above rat-derived desacyl ghrelin was contained per vial.

Male Wistar rats (9 to 10 weeks old) were used as experimental animals.

Next, 0.1 mg of the rat-derived desacyl ghrelin was dissolved in 0.6 mL of physiological saline and the solution was administered to the animals.

The administration to the animals was performed by a single dose of intraperitoneal or intracerebroventricular injection. The dose was 3 nmol/rat for intraperitoneal administration and 0.5 nmol/rat for intracerebroventricular administration, regardless of the weight of the animals. The weight of the rats varied from 350.2 to 375.8 g.

The back or tail surface temperature of the animals was measured for 1 hour at intervals of 1 minute by thermography using FLIR SC620 (software name: FLIR Rsearch IR) made by FLIR Systems Inc. The body temperature values measured by thermography are shown as increase and decrease from the zero reference point obtained by measurement of the body temperature for 10 minutes prior to the intraperitoneal injection.

The rectal temperature was measured with a small animal body temperature controller ATC-101B made by Unique Medical Co., Ltd.

The life or death of each animal was determined in a comprehensive manner based on changes in the heart rate, respiratory rate, and body temperature, the amount of activity, the response to a physical stimulation, etc.

The laboratory was maintained at room temperature and the rats were carried thereinto. The rat-derived desacyl ghrelin was intraperitoneally injected to the rats in an amount of 3 nmol/rat. As a control, 3 nmol/rat of a rat-derived ghrelin (a peptide compound of SEQ ID NO: 14 in which the hydroxyl group of the side chain of the serine residue located at position 3 from the amino terminus is acylated with an n-octanoyl group) (chemically synthesized by Peptide Institute, Inc. and prepared in the same manner as in the preparation of the desacyl ghrelin) was intraperitoneally injected to the rats. As another control, 200 µl/rat of physiological saline was intraperitoneally injected to the rats.

Similarly, 0.5 nmol/rat of the rat-derived desacyl ghrelin was intracerebroventricularly administered to the rats. As a control, 0.5 nmol/rat of the rat-derived ghrelin was intracerebroventricularly administered the rats. As another control, 200 µl/rat of physiological saline was intracerebroventricularly administered to the rats.

Figure 2:
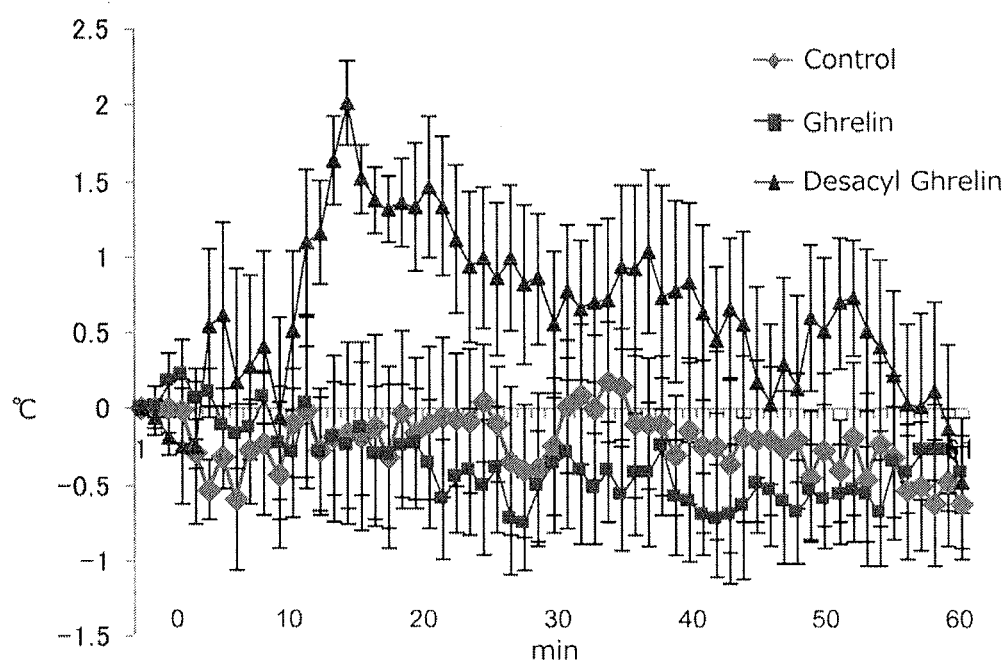
FIG. 2 is a chart showing the hypothermic effect of desacyl ghrelin that is intraperitoneally administered to rats with the normal body temperature. The triangle symbol represents the administration of desacyl ghrelin, the square symbol represents the administration of ghrelin, and the diamond symbol represents the administration of physiological saline. The vertical axis represents the changes in the tail surface body temperature (° C.) of the rats and the horizontal axis represents the elapsed time (minutes) after injection. The tail surface body temperature at the time of injection (zero minutes) is 32.6 to 34.4° C.
Figure 3:
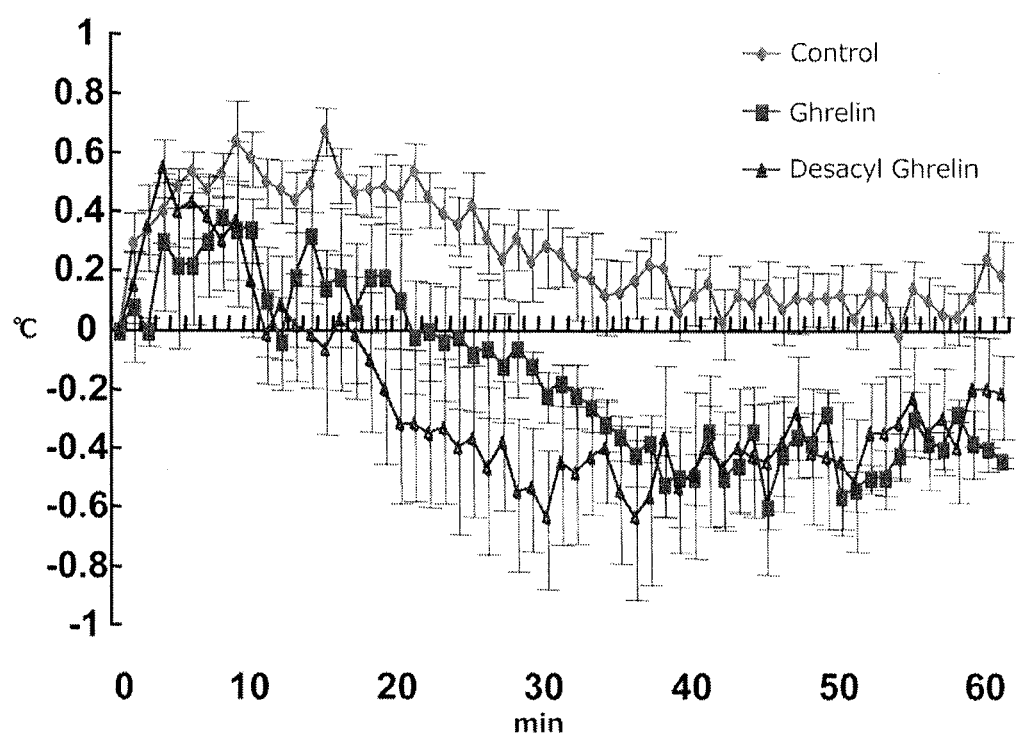
FIG. 3 is a chart showing the hypothermic effect of desacyl ghrelin that is intracerebroventricularly administered to rats with the normal body temperature. The triangle symbol represents the administration of desacyl ghrelin, the square symbol represents the administration of ghrelin, and the diamond symbol represents the administration of physiological saline. The vertical axis represents the changes in the back surface body temperature (° C.) of the rats and the horizontal axis represents the elapsed time (minutes) after injection. The back surface temperature at the time of injection (zero minutes) is 37.6 to 39.2° C.

The back and tail surface temperatures were measured by thermography in this Example. The results are shown in FIGS. 1, 2, and 3.

The back surface temperature of the desacyl ghrelin-administered group was 0.3 to 0.8° C. lower than that of the physiological-saline administered group 5 to 60 minutes after the intraperitoneal injection (FIG. 1). The tail surface temperature was increased by the administration of desacyl ghrelin, which revealed that the heat dissipation effect of desacyl ghrelin is more excellent than that of ghrelin (FIG. 2). The desacyl ghrelin-administered group showed a higher hypothermic effect in back surface temperature than that in the ghrelin-administered group 10 to 30 minutes after the intracerebroventricular injection (FIG. 3).

These results revealed that the administration of desacyl ghrelin immediately lowers the body temperature of an animal with the normal body temperature.

Example 2

Suppressive Effect of Desacyl Ghrelin Against Body Temperature Increase in Rats with Hyperthermia This experiment was performed in the same manner as in Example 1 unless otherwise stated.

While maintaining the air temperature in the laboratory at 33 to 35° C., the humidity was increased from 30% (at the beginning of the experiment) to 75% (at the end of the experiment), and thus the laboratory conditions were gradually changed to high temperature and high humidity conditions. The rats were then carried into the laboratory. The rats were housed in a plastic cage in groups of three each. Thirty minutes after carrying the rats in the high-temperature laboratory, 10 nmol/rat of the rat-derived desacyl ghrelin was intraperitoneally injected to the rats. As a control, 200 μl/rat of physiological saline was intraperitoneally injected to the rats.

At the elapsed time of 110 minutes (80 minutes after the intraperitoneal injection), the rats were transferred from the laboratory to room temperature.

At the elapsed time of 130 minutes (100 minutes after the intraperitoneal injection), the life or death of each rat was determined by visual observation and palpation.

The body temperature was measured at the rectum in this Example. The results are shown in Table 1.

TABLE 1

| Elapsed time (minutes) | Body temperature of rats (° C.) | | Statistical analysis | Note |
|---|---|---|---|---|
| | Control group | Desacyl ghrelin-administered group | | |
| 0 | 36.1 ± 0.4 | 36.1 ± 0.1 | ND | |
| 10 | 37.0 ± 0.6 | 37.0 ± 0.1 | ND | |
| 20 | 37.9 ± 0.5 | 38.2 ± 0.2 | ND | |
| 30 | 38.8 ± 0.5 | 38.8 ± 0.2 | ND | Intraperitoneal injection |
| 40 | 39.4 ± 0.1 | 39.2 ± 0.2 | ND | |
| 50 | 40.1 ± 0.1 | 39.7 ± 0.0 | p < 0.01 | |
| 60 | 40.2 ± 0.2 | 39.9 ± 0.1 | p < 0.05 | |
| 70 | 40.6 ± 0.3 | 40.0 ± 0.3 | p < 0.05 | |
| 80 | 40.7 ± 0.5 | 40.2 ± 0.2 | p < 0.05 | |
| 90 | 40.9 ± 0.3 | 40.0 ± 0.2 | p < 0.05 | |
| 100 | 41.3 ± 0.4 | 40.1 ± 0.2 | p < 0.05 | |
| 110 | 41.3 ± 0.4 | 40.3 ± 0.1 | p < 0.05 | Rats were transferred to room temperature. |

At the elapsed time of 30 minutes, the body temperature of the rats increased to about 39° C. and their activities decreased. During the elapsed time of 50 minutes (20 minutes after the intraperitoneal injection) to 110 minutes (80 minutes after the intraperitoneal injection), the body temperature of the rats of the desacyl ghrelin-administered group was 0.3 to 1.2° C. lower than that of the physiological saline-administered group (p<0.05 or 0.01). At the elapsed time of 130 minutes (100 minutes after the intraperitoneal injection), two of the three rats died in the control group, whereas all the three rats in the desacyl ghrelin-administered group survived.

These results revealed that the administration of desacyl ghrelin can suppress an increase in the body temperature of an animal with hyperthermia such as heat illness etc. Also revealed is that the administration of desacyl ghrelin improves the survival rate of an animal with hyperthermia such as heat illness etc.

INDUSTRIAL APPLICABILITY

As described above, an agent of the present invention comprising, as an active ingredient, desacyl ghrelin or its derivative, or a pharmaceutically acceptable salt thereof can be administered to various animals to exert a hypothermic effect on the animals and is therefore industrially useful.

The invention claimed is:

1. A method of lowering the body temperature of an animal having normal body temperature and in need of having its body temperature lowered, the method comprising administering desacyl ghrelin or its derivative, or a pharmaceutically acceptable salt thereof to the animal.

2. The method according to claim 1, wherein the desacyl ghrelin or its derivative is selected from the group consisting of:
  (1) a peptide having an amino acid sequence of any of SEQ ID NOs: 1 to 18;
  (2) a peptide having an amino acid sequence of any of SEQ ID NOs: 1 to 18 in which the sequence of the N-terminus to the fourth amino acid is retained at the N-terminal side, and 1 to 24 amino acids in the sequence of the fifth amino acid to the C-terminus are subjected to deletion, substitution and/or addition;
(3) a peptide of (2) in which one or two basic amino acids are added to the C-terminus; and
(4) a peptide of (2) or (3) in which the C-terminus of the amino acid sequence is amidated.

3. The method according to claim 2, wherein the basic amino acid is lysine or arginine.

4. The method according to claim 1, wherein the desacyl ghrelin or its derivative, or a pharmaceutically acceptable salt thereof, is administered in an amount of 0.001 mg to 1000 mg per dose unit.

5. The method according to claim 1, wherein the administration method is intravenous, intraperitoneal, subcutaneous, or intramuscular injection.

* * * * *